(12) United States Patent
Baer et al.

(10) Patent No.: US 7,239,389 B2
(45) Date of Patent: Jul. 3, 2007

(54) DETERMINATION OF IRRADIATION PARAMETERS FOR INSPECTION OF A SURFACE

(75) Inventors: Adam Baer, Rehovot (IL); Ditza Auerbach, Aseret (IL)

(73) Assignee: Applied Materials, Israel, Ltd., Rehovot (IL)

(*) Notice: Subject to any disclaimer, the term of this patent is extended or adjusted under 35 U.S.C. 154(b) by 314 days.

(21) Appl. No.: 10/903,125

(22) Filed: Jul. 29, 2004

(65) Prior Publication Data

US 2006/0244976 A1 Nov. 2, 2006

(51) Int. Cl.
*G01J 4/00* (2006.01)
*G01N 21/00* (2006.01)
*G06F 17/18* (2006.01)

(52) U.S. Cl. .................... 356/369; 702/179; 356/237.2

(58) Field of Classification Search ........ 356/365–369, 356/273.2, 237.2; 702/179, 194
See application file for complete search history.

(56) References Cited

U.S. PATENT DOCUMENTS

| | | | | |
|---|---|---|---|---|
| 4,884,886 A | * | 12/1989 | Salzman et al. | ............ 356/367 |
| 5,076,696 A | * | 12/1991 | Cohn et al. | .................. 356/369 |
| 5,333,052 A | * | 7/1994 | Finarov | ...................... 356/369 |
| 5,424,536 A | * | 6/1995 | Moriya | ....................... 250/225 |
| 5,604,591 A | | 2/1997 | Kitagawa | |
| 5,883,710 A | * | 3/1999 | Nikoonahad et al. | .... 356/237.2 |
| 5,900,939 A | * | 5/1999 | Aspnes et al. | ............... 356/369 |
| 6,034,776 A | * | 3/2000 | Germer et al. | ............... 356/369 |
| 6,078,834 A | | 6/2000 | Lurie | |
| 6,081,325 A | * | 6/2000 | Leslie et al. | .............. 356/237.2 |
| 6,122,047 A | * | 9/2000 | Stover et al. | ............. 356/237.3 |
| 6,169,601 B1 | * | 1/2001 | Eremin et al. | ............... 356/239.8 |
| 6,215,551 B1 | * | 4/2001 | Nikoonahad et al. | .... 356/237.2 |
| 6,236,880 B1 | * | 5/2001 | Raylman et al. | ............. 600/436 |
| 6,288,780 B1 | * | 9/2001 | Fairley et al. | ............ 356/237.1 |
| 6,369,375 B1 | | 4/2002 | Ishiwata | |
| 6,731,384 B2 | * | 5/2004 | Ohshima et al. | .......... 356/237.2 |
| 7,068,363 B2 | * | 6/2006 | Bevis et al. | .............. 356/237.5 |
| 2002/0179867 A1 | * | 12/2002 | Fielden et al. | ............ 250/559.45 |
| 2003/0184744 A1 | * | 10/2003 | Isozaki et al. | ............ 356/237.2 |
| 2004/0125375 A1 | * | 7/2004 | Some | .......................... 356/369 |
| 2004/0150820 A1 | * | 8/2004 | Nikoonahad et al. | ........ 356/364 |
| 2004/0233444 A1 | * | 11/2004 | Mieher et al. | ............... 356/401 |

* cited by examiner

*Primary Examiner*—Layla G. Lauchman
*Assistant Examiner*—Bryan Giglio
(74) *Attorney, Agent, or Firm*—Tarek N. Fahmi

(57) ABSTRACT

Apparatus for inspection of a surface, including irradiating optics which are adapted to irradiate the surface with an irradiating beam having an adjustable polarization. The apparatus further includes at least one detector, each detector being associated with a respective analyzer having an orientation and adapted to generate signals in response to light received via the analyzer from an irradiated area on the surface, one of the at least one detector being adapted to receive scattered light from the irradiated area. The apparatus also includes a controller which is adapted to direct the irradiating optics to irradiate the irradiated area and which, in response to calibration signals generated thereby at the at least one detector, is adapted to set the adjustable polarization and the orientation of the respective analyzer of each detector.

27 Claims, 3 Drawing Sheets

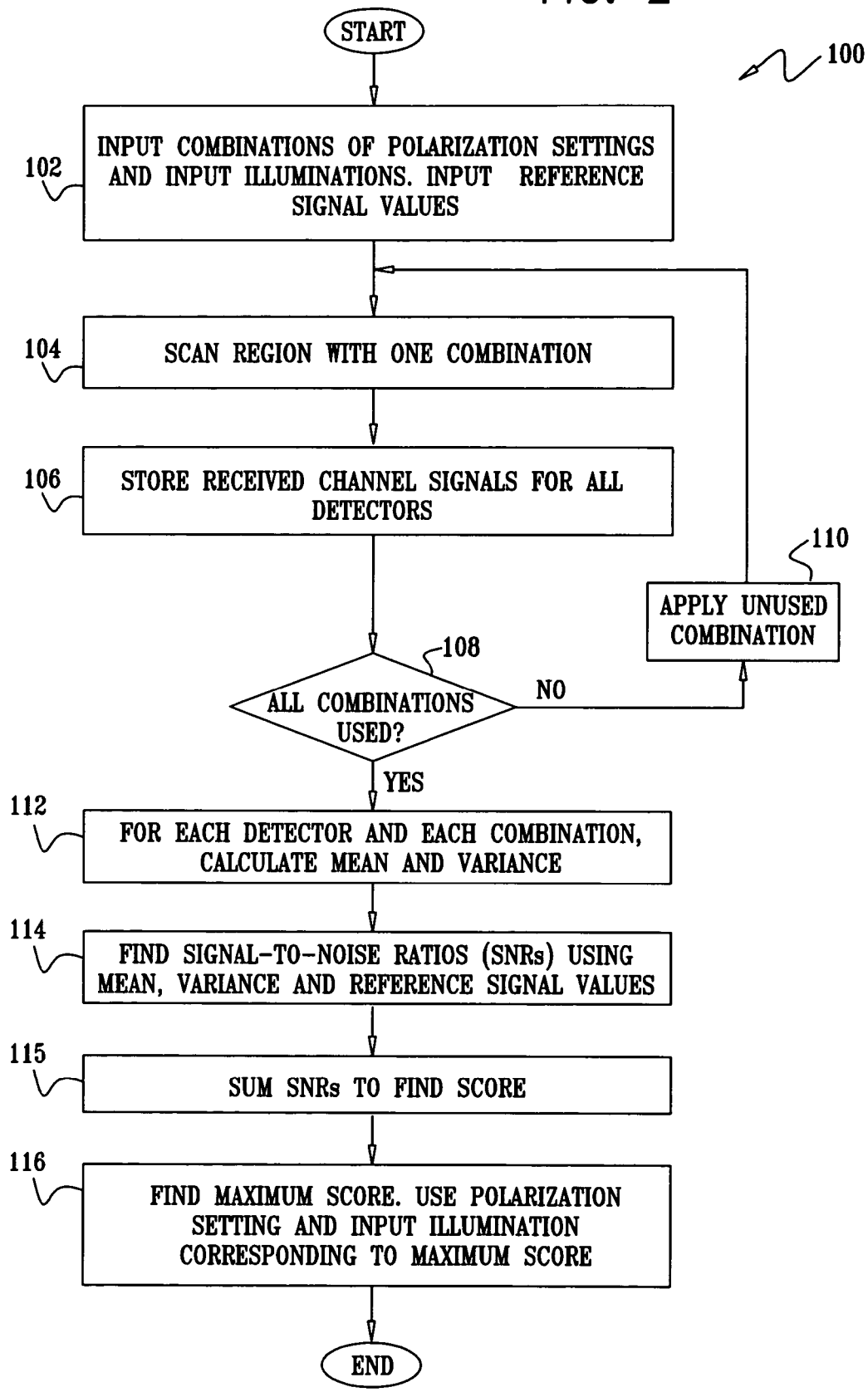

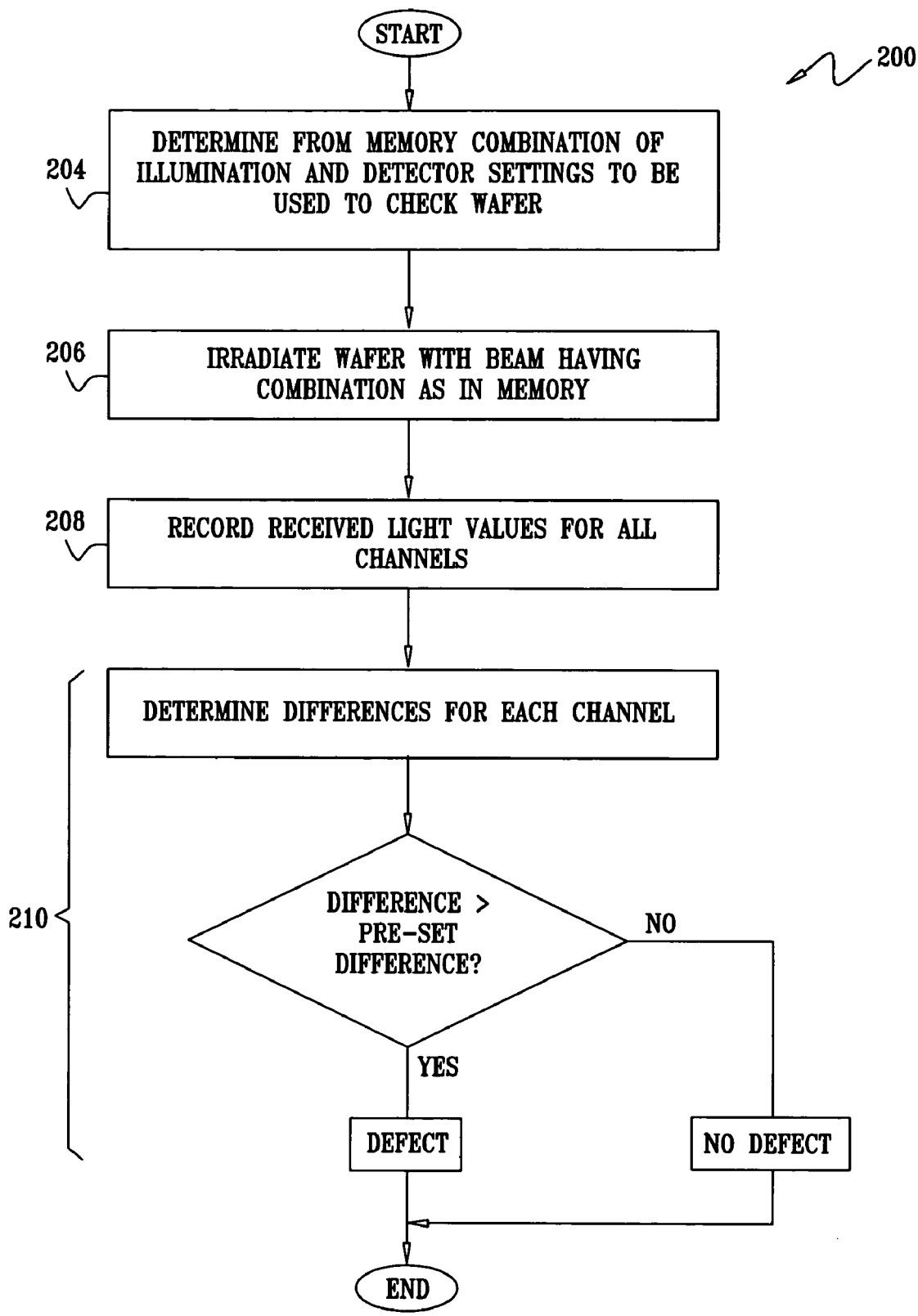

DETERMINATION OF IRRADIATION PARAMETERS FOR INSPECTION OF A SURFACE

FIELD OF THE INVENTION

The present invention relates generally to defect inspection devices, and specifically to defect inspection devices using polarized light.

BACKGROUND OF THE INVENTION

Detecting defects on the surface of wafers produced in the semi-conducting industry is a critical part of the whole production process. Efficient detection includes the ability to distinguish between apparent defects, which may include "nuisance" effects or false alarms, and actual defects. Nuisance effects may include conductors having irregular edges and/or cross-sections. Actual defects include shorts between conductors and breaks of a conductor. Detection systems known in the art include "bright field" systems, using specularly reflected radiation from the wafer surface, and "dark field" systems, which use the scattered radiation from the surface. A number of systems known in the art use specific polarizations of the beam irradiating the wafer surface, or polarizing elements in the detection system.

U.S. Pat. No. 5,883,710, to Nikoonahad et al., U.S. Pat. No. 6,081,325, to Leslie et al., and U.S. Pat. No. 6,215,551, to Nikoonahad et al., whose disclosures are incorporated herein by reference, describe surface inspection systems where an incident beam is directed at a low or grazing angle relative to the surface of the wafer. The incident beam may be set to have s, p, left-, or right-handed circular polarization.

U.S. Pat. No. 6,288,780, to Fairley et al., whose disclosure is incorporated herein by reference, describes a wafer inspection system which is able to use either or both a bright field and a dark field image. The bright field is generated by an unpolarized arc lamp. The system includes a dark field illumination module comprising two laser illumination beams, having adjustable grazing angle, light level, and polarizations.

U.S. Patent Application 2003-0184744 to Isozaki et al., whose disclosure is incorporated herein by reference, describes a surface inspection method that illuminates a region with one or two fixed laser beams, so as to illuminate the region at two different angles. A detection system includes a polarizing plate which may be rotated to maximize a signal/noise ratio.

SUMMARY OF THE INVENTION

In embodiments of the present invention, a region on a wafer is irradiated by an incident beam, typically a normally-incident beam, having a known, adjustable polarization. One or more detectors, associated with respective analyzers having adjustable orientations, are configured to measure light from the irradiated region, and at least one of the detectors measures scattered light from the irradiated region. Typically, one of the detectors measures specular light from the region. A controller sets the polarization of the incident beam and the orientations of the analyzers.

The region typically comprises an irradiated area which is used as a reference region, so as to provide optimized settings for the beam polarization and the analyzer orientations for other regions of the wafer. The optimized settings are chosen so as to maximize a signal to noise ratio (SNR) of the signals (in this case, calibration signals) that are generated by the one or more detectors. The optimized settings are then used in irradiating the other regions of the wafer and/or other wafers being tested for defects. The combination of an incident beam with an optimized polarization and detectors with optimized analyzer orientations leads to a high detection efficiency for defects, with a low false-alarm rate.

There is therefore provided, according to an embodiment of the present invention, apparatus for inspection of a surface, including:

irradiating optics which are adapted to irradiate the surface with an irradiating beam having an adjustable polarization;

at least one detector, each detector being associated with a respective analyzer having an orientation and adapted to generate signals in response to light received via the analyzer from an irradiated area on the surface, one of the at least one detector being adapted to receive scattered light from the irradiated area; and a controller which is adapted to direct the irradiating optics to irradiate the irradiated area and which, in response to calibration signals generated thereby at the at least one detector, is adapted to set the adjustable polarization and the orientation of the respective analyzer of each detector.

Typically, the at least one detector includes a bright field detector preceded by a bright field analyzer having a bright field analyzer orientation that is adapted to reduce a level of the signals generated by the bright field detector.

In an embodiment, the irradiating optics include a linear polarizer, a half-wave plate, and a quarter-wave plate, which are oriented under direction of the controller to generate multiple polarizations, and the adjustable polarization is chosen from one of a linear polarization, a circular polarization, and an elliptical polarization.

In one embodiment, the at least one detector includes a gray field detector adapted to receive the scattered light from a near normal field, wherein the near normal field includes a solid angle subtending an angle greater than approximately 2° and less than approximately 45° to a normal to the surface. Alternatively or additionally, the at least one detector includes a dark field detector adapted to receive the scattered light from a far field, wherein the far field includes a solid angle forming an angle greater than approximately 5° and less than approximately 37° with the surface.

Typically, the controller is adapted to calculate a mean and a variance of the signals generated by each detector, and to calculate a signal-to-noise ratio (SNR) for each detector in response to the mean and the variance. In a disclosed embodiment, the controller is adapted to receive reference signal values generated by a non-polarizing defect, and to calculate the SNR in response to the reference signal values. The controller may be adapted to generate multiple SNR values in response to multiple polarizations generated in the irradiating beam, and in response to respective orientations of each analyzer, and is typically further adapted to determine a sum of the multiple SNR values. Furthermore, the controller may be adapted to determine a maximum value of the sum, and in response thereto is typically adapted to determine an optimized illumination polarization setting for the irradiating beam, and a respective optimized detector analyzer setting for each respective analyzer.

In a disclosed embodiment, the controller is adapted to detect a defect on the surface by directing the irradiating optics to irradiate the surface at the adjustable polarization, and by setting the orientation of the respective analyzer of each detector.

In some embodiments, the irradiating beam is substantially normally incident to the surface.

There is further provided, according to an embodiment of the present invention, a method for inspection of a surface, including:

irradiating the surface with an irradiating beam having an adjustable polarization;

receiving light from an irradiated area on the surface in at least one detector, each detector being associated with a respective analyzer having an orientation and generating signals in response to the light received via the analyzer from the irradiated area, one of the at least one detector being adapted to receive scattered light from the irradiated area; and irradiating the irradiated area of the surface and, in response to calibration signals generated thereby at the at least one detector, setting the adjustable polarization and the orientation of the respective analyzer of each detector.

Typically, the at least one detector includes a bright field detector preceded by a bright field analyzer, and the method further includes setting the orientation of the bright field analyzer to reduce a level of the signals generated by the bright field detector.

In an embodiment, irradiating the surface includes orienting a linear polarizer, a half-wave plate, and a quarter-wave plate, to generate multiple polarizations, and the adjustable polarization may be chosen from one of a linear polarization, a circular polarization, and an elliptical polarization.

In one embodiment, the at least one detector includes a gray field detector adapted to receive the scattered light from a near normal field, wherein the near normal field includes a solid angle subtending an angle greater than approximately 2° and less than approximately 45° to a normal to the surface. Alternatively or additionally, the at least one detector includes a dark field detector adapted to receive the scattered light from a far field, wherein the far field includes a solid angle forming an angle greater than approximately 5° and less than approximately 37° with the surface.

A disclosed embodiment includes calculating a mean and a variance of the signals generated by each detector, and calculating a signal-to-noise ratio (SNR) for each detector in response to the mean and the variance, and may additionally include providing reference signal values generated by a non-polarizing defect, wherein calculating the SNR includes calculating the SNR in response to the reference signal values. Optionally, the disclosed embodiment includes generating multiple SNR values in response to multiple polarizations generated in the irradiating beam, and in response to respective orientations of each analyzer, and determining a sum of the multiple SNR values. The disclosed embodiment may further include determining a maximum value of the sum, and in response thereto determining an optimized illumination polarization setting for the irradiating beam, and a respective optimized detector analyzer setting for each respective analyzer.

In some embodiments, the method includes detecting a defect on the surface by directing the irradiating beam to irradiate the surface at the adjustable polarization, and by setting the orientation of the respective analyzer of each detector.

In an alternative embodiment, the irradiating beam is substantially normally incident to the surface.

There is further provided, according to an embodiment of the present invention, a method for determining irradiation parameters for a surface, including:

arranging an irradiation system to irradiate the surface, the system including an illumination source having a first adjustable polarizer between the source and the surface and at least one detector having respective second adjustable polarizers between the at least one detector and the surface;

operating the system at each of a plurality of different settings of the polarizers so as to generate signals at the at least one detector responsively to light from the surface;

responsively to the signals, computing a respective score indicative of the plurality of settings; and selecting one of the settings for use in inspection of the surface with the system, responsively to the respective score.

In one embodiment, the first adjustable polarizer includes an adjustable half-wave plate and an adjustable quarter-wave plate. Typically, the respective second adjustable polarizers include analyzers which act to filter incident light.

In an embodiment, computing the respective score includes calculating a plurality of signal-to-noise ratios (SNRs) for the signals at the at least one detector, and determining a sum of the SNRs. The embodiment may also include determining a maximum value of the sum, wherein selecting one of the settings includes selecting the setting in response to the maximum value.

There is further provided, according to an embodiment of the present invention, apparatus for determining irradiation parameters for a surface, including:

an illumination source having a first adjustable polarizer between the source and the surface;

at least one detector having respective second adjustable polarizers between the at least one detector and the surface; and a controller which is adapted to:

operate the illumination source and the at least one detector at each of a plurality of different settings of the polarizers so as to generate signals at the at least one detector responsively to light from the surface, responsively to the signals, compute a respective score indicative of the plurality of settings, and select one of the settings for use in inspection of the surface, responsively to the respective score.

Typically, the first adjustable polarizer includes an adjustable half-wave plate and an adjustable quarter-wave plate, and the respective second adjustable polarizers include analyzers which act to filter incident light.

In an embodiment, the controller is adapted to calculate a plurality of signal-to-noise ratios (SNRs) for the signals at the at least one detector, and determine a sum of the SNRs. In the embodiment, the controller may additionally be adapted to determine a maximum value of the sum, and to select the one of the settings in response to the maximum value.

The present invention will be more fully understood from the following detailed description of the preferred embodiments thereof, taken together with the drawings, a brief description of which follows.

BRIEF DESCRIPTION OF THE DRAWINGS

FIG. 2 is a flow chart of a process showing steps performed in determining polarization settings to be used when regions of a surface are irradiated, according to an embodiment of the present invention; and FIG. 3 is a flow chart of a process showing steps performed in scanning a wafer for defects, according to an embodiment of the present invention.

DETAILED DESCRIPTION OF EMBODIMENTS

Figure 1:
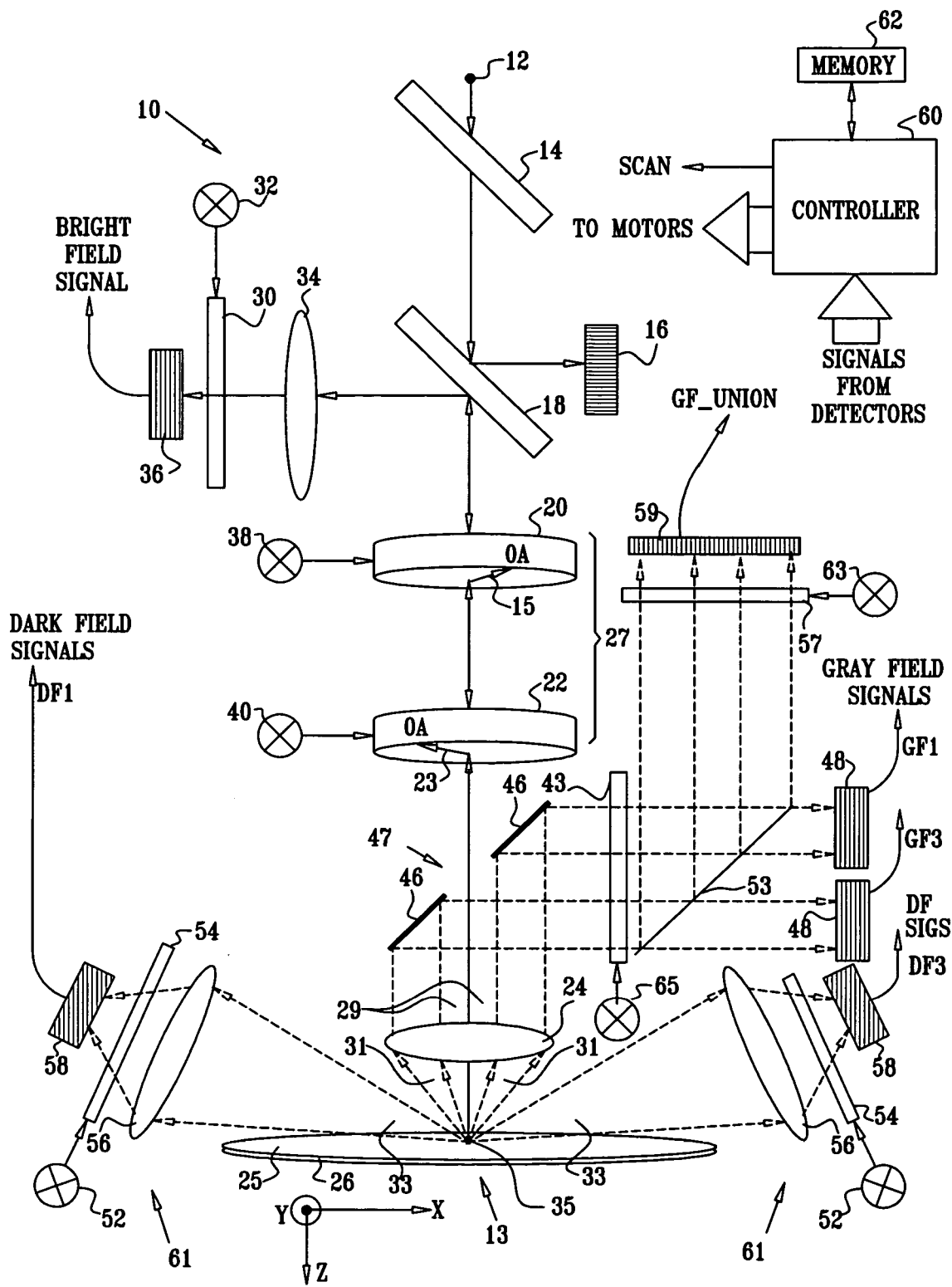
FIG. 1 is a schematic illustration of optical inspection apparatus, according to an embodiment of the present invention.

Reference is now made to FIG. 1, which is a schematic illustration of optical inspection apparatus 10, according to an embodiment of the present invention. Apparatus 10 comprises an illumination source 12, typically a laser source, which as is described in more detail below is adapted to generate a light beam that is focused to a spot 13, typically using an auto-focus system, on a surface 25 of a wafer 26. Apparatus 10 thus acts as an irradiation system to irradiate surface 25. In an embodiment, source 12 comprises a solid state diode laser generating continuous radiation at 532 nm. Unless otherwise stated herein, surface 25 is assumed to lie in an x-y plane, where an x-axis is in the plane of the paper, and a y-axis is out of the plane of the paper. Thus, light from source 12 to spot 13 is generally parallel to a z-axis, i.e., is typically incident normally to surface 25. Apparatus 10 is used to inspect surface 25, by having spot 13 traverse the surface of the wafer. Methods for scanning spot 13 across surface 25 are known in the art. Typically the methods incorporate devices, such as acousto-optic modulators, which may be coupled to move the spot, the wafer, or both, in a controlled manner. The scan devices are controlled by a controller 60, which also controls the operation of apparatus 10. For clarity, devices for scanning spot 13 across surface 25, and for automatically focusing the spot onto the surface, are omitted from FIG. 1.

U.S. Patent Application 2004/0125375 to Some, which is assigned to the assignee of the present invention, and which was published after the present invention was reduced to practice, describes methods for scanning as well as methods for detecting defects in a wafer during the scanning.

To produce spot 13, light from source 12 is passed through a linear polarizer 14, which typically has an extinction ratio better than 200:1 and a transmission better than 98% for the transmitted linearly polarized light it produces. Polarizer 14 may advantageously be implemented from a glass plate set at the Brewster angle for the glass. Polarizer 14 outputs linearly polarized light in a direction in the x-y plane, the polarization direction hereinbelow, unless otherwise stated, being assumed to be parallel to the x-axis.

The linearly polarized light from polarizer 14 passes through a non-polarizing beam splitter 18, which typically reflects approximately 20% of the incident light to a beam dump 16, and transmits approximately 80% of the incident light as linearly polarized light to a quarter-wave plate 20. The inventors have found that the 80/20 transmission/reflection ratio for beam splitter 18 provides a satisfactory compromise between reflected light requirements of an auto-focus system and preference for maximum power on the wafer. It will be appreciated, however, that any other suitable transmission/reflection ratio may be used. Plate 20 is oriented so that its mechanical axis of symmetry, normal to the plane of the plate, is typically tilted at about 5° to the z-axis, to prevent stray reflections interfering with the operation of apparatus 10. The plate is coupled to a motor 38 that is controlled by controller 60, so that the motor is able to orient the plate in a controlled manner about its axis.

An optic axis 15 of plate 20 lies in the plane of the plate. Depending on the angle made by optic axis 15 with the polarization direction—the x-axis—of the incoming light, and assuming the angle to be non-zero, motor 38 may set the light exiting from the plate to be left- or right-circularly or elliptically polarized. If the angle made by optic axis 15 with the polarization direction is zero, then the light exiting plate 20 is linearly polarized along the x-axis.

The light exiting from plate 20 is transmitted to a half-wave plate 22, oriented with its mechanical axis, normal to the plane of the plate, typically tilted at about 5° to the z-axis to neutralize the effect of stray reflections. Plate 22 is coupled to a motor 40 that is controlled by controller 60 and that is able to orient the plate about its axis. An optic axis 23 of plate 22 lies in the plane of the plate. Half-wave plate 22 acts on light incident on the plate according to the type of polarization of the incident light, and according to the angle made by the direction of polarization of the incident light with optic axis 23. If the incident light is linearly polarized, plate 22 rotates the direction of polarization by $2\theta$, where $\theta$ is the angle between the plate's optic axis and the incident light's direction of polarization. If the incident light is elliptically polarized, plate 22 rotates the axes of the ellipse by $2\theta$.

The effective angle of polarization ($\theta$) and ellipticity e of the radiation exiting the combination of plates 20 and 22 are given by equations (1):

$$\theta = 2\varphi_{\frac{\lambda}{2}} - \varphi_{\frac{\lambda}{4}}$$

$$e = \begin{cases} \left|\tan\left(\varphi_{\frac{\lambda}{4}}\right)\right| & 0 \leq \varphi_{\frac{\lambda}{4}} < 45 \\ \left|\tan\left(90 - \varphi_{\frac{\lambda}{4}}\right)\right| & 45 \leq \varphi_{\frac{\lambda}{4}} < 90 \end{cases} \quad (1)$$

where $$\varphi_{\frac{\lambda}{4}} \text{ and } \varphi_{\frac{\lambda}{2}}$$

are the respective angles between the half-wave plate and quarter-wave plate fast axes and the incoming polarization orientation.

It will be appreciated that the combination of rotatable quarter-wave plate 20 and rotatable half-wave plate 22 gives complete control over the type of polarization of light transmitted from the half-wave plate, given incident linearly polarized light. The combination is also referred to hereinbelow as polarization controlling mechanism 27. It will also be appreciated that mechanism 27 acts as an adjustable polarizer between source 12 and surface 25. It will further be appreciated that while the description of mechanism 27 refers to rotation of half and quarter wave plates, electro-optic materials or other electrically active retarders may be used in place of plates 20 and 22 to provide the same continuously variable polarization as is provided by mechanism 27. Those skilled in the art will appreciate that mechanism 27, and any other system used to generate continuously variable polarization, has to meet certain system constraints, such as ability to withstand high radiation power densities generated by the irradiating source.

Light from plate 22 is focused by an objective 24 to spot 13, so as to irradiate a region 35 of surface 25. It will be understood that the light irradiating region 35 has substantially the same polarization as that output by polarization controlling mechanism 27.

Apparatus 10 divides light radiating from region 35 into three fields. A first bright field 29 receives light that is substantially specularly reflected from region 35. The substantially specularly reflected light is collimated by objective 24, and passes through a hole 47 in a mirror 46. The function of mirror 46 is described below. The light then traverses plate 22 and plate 20, striking beam splitter 18. Beam splitter 18 reflects approximately 20% of the light incident on the beam splitter, via focusing optics 34, to a bright field analyzer 30, the orientation of which is controlled via controller 60 by a motor 32. Analyzer 30, and other analyzers referred to herein, act as adjustable polarizers to filter and linearly polarize incident light, as is known in the art. The light is focused onto a bright field detector 36, and the output from detector 36 is transferred as a bright field channel signal to controller 60 for analysis, as described in more detail below.

It will be understood that specularly reflected light from region 35 arriving at analyzer 30 is, to a first approximation, linearly polarized in a direction depending on the orientation of quarter-wave plate 20. Thus, analyzer 30 may be oriented to filter out substantially all the specularly reflected light from region 35.

A second near normal field 31, also herein termed a gray field, receives light that is scattered from region 35 at angles between more than approximately 2° and less than approximately 45°, the angles being measured with respect to the normal to surface 25, and defining a solid angle that field 31 subtends. Light in gray field 31 is collimated by objective 24 and is then reflected from mirror 46.

The light reflected from mirror 46 passes through a first gray field analyzer 43 to an approximately 50/50 non-polarizing beam-splitter 53. Analyzer 43 is driven by a motor 65. The transmitted light from beam-splitter 53 is directed to four substantially similar gray field detectors 48 (for clarity only two are shown in FIG. 1), each detector 48 receiving light from approximately one quarter of field 31. The reflected light from beam-splitter 53 is directed via a second gray field analyzer 57 to a second gray field detector 59. Analyzer 57 is driven by a motor 63. For clarity, collimation and focusing optics between mirror 46 and detectors 48 and 59 are not shown in FIG. 1.

Typically, in operation of apparatus 10, either analyzer 57 or analyzer 43 is positioned as described above. In a first configuration of apparatus 10, analyzer 43 is in position (so that analyzer 57 is not in position), and all five gray field detectors receive the same type of polarized light. In a second configuration of apparatus 10, analyzer 57 is in position (so that analyzer 43 is not in position), and only detector 59 receives polarized light. The output signals of detectors 48 are herein termed GF1, GF2, GF3, and GF4, and the output signal of detector 59 is herein termed GF_UNION.

In a disclosed embodiment, controller 60 receives GF1, GF2, GF3, GF4, and GF_UNION as five gray field channels.

A third far field 33, also herein termed a dark field, receives light, herein termed dark field light, that is scattered from region 35 at angles to surface 25 that are between approximately 5° and approximately 37°, the angles defining a solid angle that field 33 subtends. The dark field light transmits, via focusing optics 56 and through one or more dark field analyzers 54, each analyzer having an orientation set by a respective motor 52, under the control of controller 60. The dark field light is focused to a respective dark field detector 58. The output from each detector 58 is transferred to controller 60. Each motor 52, polarizer 54, dark field optics 56 and detector 58 is herein collectively termed dark field detection system 61. For clarity, FIG. 1 only shows two dark field detection systems 61. Typically, apparatus 10 comprises more than one system 61.

In the disclosed embodiment referred to above, there are four dark field detection systems 61, each of the systems being disposed symmetrically with respect to region 35, typically in azimuth directions corresponding to the four gray field channels. Thus, each system 61 receives scattered light from a portion of the dark field. The output signals of detectors 58 are termed DF1, DF2, DF3, and DF4 and are transmitted to controller 60 as four dark field channels.

Controller 60 acts as a central processing unit for apparatus 10, providing signals to set motors 32, 38, 40, 63, 65, and 52 as it scans spot 13 over surface 25, the motor settings being described in more detail below. Controller 60 typically comprises one or more analog-digital (A/D) converters which convert analog signals generated by detectors 36, 48, 59, and 58, and/or sums from the detectors as described above, to digital values, which are in turn stored in a memory 62 coupled to the controller.

As stated above, apparatus 10 may be used to scan surface 25 so as to locate defects on the surface. A defect typically comprises, but is not limited to, an extraneous particle on surface 25, a contaminant on the surface, a short between conductors on the surface, and a break in a conductor. The defect typically causes a difference in polarization characteristics of light radiating from the region of the defect, compared to the polarization characteristics of light radiating from the same region if no defect is present. The polarization characteristics of light from such a "non-defect region" are typically a function of the polarization characteristics of the irradiating light and of the region itself. For example, if the region comprises a patterned region made up of relatively closely spaced parallel conductors, the parallel conductors influence the polarization characteristics of the light from the region. Other factors which influence the polarization characteristics of light from the region will be apparent to those skilled in the art.

FIG. 2 is a flow chart of a process 100 showing steps performed in determining polarization settings to be used when regions of surface 25 are irradiated, according to an embodiment of the present invention. Surface 25 typically comprises a large number of substantially identical dies. In process 100, a region of the surface, typically comprising one or more dies, is an irradiated area, hereinbelow also referred to as a reference region, which is used to determine optimized settings for apparatus 10 to scan the rest of surface 25 and/or surfaces of other wafers similar to wafer 26. The settings comprise the orientations of plate 20, plate 22, analyzer 30, analyzers 43 and 57, and analyzers 54.

In the description below, process 100 is described with reference to the disclosed embodiment described above, having four dark field detection systems 61, and generating five gray field signals. The gray field analyzers are assumed to be set according to the first configuration described above. Those skilled in the art will be able to adapt the description of process 100, mutatis mutandis, to other embodiments and configurations of the present invention.

In a first step 102, the operator inputs different combinations of settings for plate 20, plate 22, analyzer 30, analyzer 43, and analyzers 54, the combinations being stored in memory 62. Settings for plates 20 and 22 typically include those settings which generate an incident beam that is circularly polarized, linearly polarized along the x axis, and linearly polarized light along the y axis, and are herein also termed illumination polarization settings. At least some settings for analyzer 30 are implemented so that, to a first order, light input to detector 36 is minimized, so that levels of signals from the detector are reduced. Typically, settings for analyzer 30 thus include those that minimize reflected light from the incident circularly or linearly polarized beam.

Gray field analyzer settings, for analyzer 43, typically include setting values which minimize the detected radiation from the incident beams described above. Gray field analyzer settings thus typically include settings which are orthogonal to the linear polarizations of the incident beam. Typical settings for analyzer 43 include the following angles (measured with respect to a reflected beam from an imaginary x-axis polarized incident beam): 0, 30, 60, 90, −30, and −60.

Dark field analyzer settings, for analyzers 54, typically include the following angles: 0, 30, 45, 60, 90, −30, and −60. As described hereinbelow, process 100 determines, inter alia, optimum values for the dark field analyzer settings.

In step 102, the operator also inputs reference non-polarizing defect signal values, (SIG(DOI), described in more detail below.

In a second step 104, apparatus 10 scans the reference region, typically using a raster scan, although any other type of scan that scans substantially all of the reference region may be used. The scan is performed at a specific combination of settings chosen by controller 60. For the scan, controller 60 sets the orientations of plate 20, plate 22, analyzer 30, analyzer 43, and analyzers 54, by setting their respective motors.

In a third step 106, for each specific irradiated area of the reference region, controller 60 determines values of channel signals measured by bright field detector 36, the four gray field detectors 48, the overall gray field detector 59, and the four dark field detectors 58. The controller stores the ten received channel values, comprising one specular reflection channel and nine scattered light channels, in memory 62.

In a decision step 108, controller 60 checks to see if all combinations of settings stored in step 102 have been used in a scan. If not, in a step 110, controller 60 applies an unused combination, and process 100 returns to step 104. If in decision step 108 all combinations have been used, process 100 continues.

In a first analysis step 112, for each detector, and for each of the different scans performed, controller 60 computes an average ($\mu$) and a variance ($\sigma$) of the values determined in step 106. Controller 60 thus computes sets of ($\mu$, $\sigma$)/detector/combination of settings. The controller may reduce the number of sets calculated using symmetry considerations between dark field detector channels DF1, DF2, DF3, and DF4, and between gray field detector channels GF1, GF2, GF3, and GF4.

In a second analysis step 114, for each set of values of ($\mu$, $\sigma$) (corresponding to one detector channel and one combination of settings), controller 60 determines a signal to noise ratio (SNR) according to equation (2):

$$SNR = \frac{SIG(DOI) - \mu}{\sigma} \quad (2)$$

where SIG(DOI) is an averaged signal from a defect of interest (DOI).

Values of SIG(DOI) are typically determined prior to performing process 100 using a non-polarizing defect on surface 25, the non-polarizing defect typically being implemented from a polystyrene latex (PSL) sphere. Values of SIG(DOI) are determined for each detector and for each combination of settings used by controller 60.

In a third analysis step 115, controller 60 determines a sum comprising SNRs over all the detectors, for each illumination polarization setting used. A value (SCORE) of the sum is determined using equation (3) below:

$$SCORE = \sum_{det} \omega_{det} \cdot [SNR]^\alpha \quad (3)$$

where [SNR] is a normalized function of SNR, $\omega_{det}$ is a weighting factor for each of the detectors, and $\alpha$ is an exponent which acts to amplify values of SNR greater than 1. Typically, $\omega_{det}$ is in a range from 0 to 1, and $\alpha$ is in a range from 1 to approximately 10.

In a final step 116, controller 60 determines a maximum value of SCORE, and the illumination polarization setting generating the maximum value, herein termed the optimized illumination polarization setting. Controller 60 then determines the detector analyzer settings, herein termed the optimized detector settings, for the optimized illumination polarization setting. The optimized settings are stored in memory 62. After completing step 116, process 100 ends.

It will be appreciated that process 100 enables controller 60 to determine optimized detector settings for all the detectors, and/or for a sub-set of the detectors. Typically, the optimized detector settings are determined for all the gray field analyzers, or for all the dark field analyzers, or for both gray field and dark field analyzers.

Controller 60 uses the optimized illumination polarization setting and the optimized detector settings, in inspecting other areas of the wafer, and/or in inspecting other wafers having surface layers similar to those of surface 25. An example of such an inspection is described with reference to FIG. 3 below.

FIG. 3 is a flow chart of a process 200 showing steps performed in scanning a wafer for defects, according to an embodiment of the present invention. Process 200 is performed after process 100 has determined respective optimized settings for the reference region. Process 200 is typically repeated for all other regions of the wafer, and may also be applied to other similar wafers. Hereinbelow the wafer being scanned is termed the "test" wafer. In the following description, process 200 is described with reference to the disclosed embodiment described above.

In a first step 204, controller 60 refers to memory 62 to set the optimized illumination polarization setting for the irradiating beam and the optimized detector settings for the analyzers, as determined step 116 of process 100.

In an irradiation step 206, controller 60 irradiates regions of the test wafer with a beam having polarization characteristics set by the optimized illumination polarization setting set in step 204.

In a results step 208, controller 60 records the values of the nine scattered light channels and the bright field channel generated by the beam irradiating the region.

In a comparison step 210, controller 60 checks the values recorded in step 208, typically using die-to-die comparisons to determine differences. If any one of the differences is greater than a respective pre-set difference, the irradiated region may be considered to indicate a defect. If none of the differences is greater than the respective pre-set differences, the irradiated region is assumed to be defect-free.

Typically, process 200 is used to generate a defect map of the test wafer.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for inspection of a surface, comprising:
    optics adapted to adjust a polarization of an irradiating beam incident on the surface;
    a bright field detector and a respective bright field analyzer, the bright field detector positioned and adapted to generate bright field signals in response to light specularly reflected from the surface and received via the bright field analyzer;
    a plurality of gray field detectors, each adapted and positioned to generate gray field signals in response to light reflected from the surface within a first angular region and received via a gray field analyzer associated with the gray field detectors;
    one or more dark field detectors, each adapted and positioned to generate dark field signals in response to light reflected from the surface within a second angular region and received via one or more respective dark field analyzers; and
    a controller adapted to receive the bright field signals, the gray field signals and the dark field signals and to determine therefrom optimized settings for one or more of the bright field detector, the plurality of gray field detectors and the one or more dark field detectors and each of the respective analyzers therefor and to control scanning of the surface using said optimized settings.

2. The apparatus according to claim 1, wherein the optics comprise a half-wave plate and a quarter-wave plate, each of which is under direction of the controller.

3. The apparatus according to claim 1, wherein the polarization of the irradiating beam is chosen from one of a linear polarization, a circular polarization, and an elliptical polarization.

4. The apparatus according to claim 1, wherein the plurality of gray field detectors are positioned to receive light from within the first angular region comprising a solid angle subtending an angle greater than 2° and less than 45° to a normal to the surface.

5. The apparatus according to claim 1, wherein the one or more dark field detectors are positioned to receive light within the second angular region comprising a solid angle forming an angle greater than or equal to 5° and less than approximately 37° with the surface.

6. The apparatus according to claim 1, wherein the controller is adapted to calculate a mean and a standard deviation of the signals from each detector, and to calculate a signal-to-noise ratio (SNR) for each detector in response to the mean and the standard deviation.

7. The apparatus according to claim 6, wherein the controller is adapted to receive reference signal values generated by a non-polarizing defect, and to calculate the SNR in response to the reference signal values.

8. The apparatus according to claim 6, wherein the controller is adapted to generate multiple SNR values in response to multiple polarizations of the irradiating beam, and in response to respective orientations of each analyzer, and wherein the controller is farther adapted to determine a sum of the multiple SNR values.

9. The apparatus according to claim 8, wherein the controller is adapted to determine a maximum value of the sum, and in response thereto to determine an optimized illumination polarization setting for the irradiating beam, and a respective optimized setting for each analyzer.

10. The apparatus according to claim 1, wherein the controller is adapted to detect a defect on the surface by directing the optics to irradiate the surface at an adjusted polarization, and by setting orientations of the analyzers.

11. The apparatus according to claim 1, wherein the irradiating beam is incident normal to the surface.

12. A method for inspection of a surface, comprising:
    controlling, using optics, polarization of an irradiating beam irradiating the surface;
    receiving light from an irradiated area on the surface at a bright field detector via a respective bright field analyzer, the bright field detector positioned and generating bright field signals in response thereto, a plurality of gray field detectors, via a gray field analyzer, and generating gray field signals in response thereto, and one or more dark field detectors, via one or more respective dark field analyzers, and generating dark field signals in response thereto; and
    optimizing, responsive to the bright field signals, the gray field signals and the dark field signals, settings for one or more of the bright field detector, the plurality of gray field detectors and the one or more dark field detectors and each of the respective analyzers therefor.

13. The method according to claim 12, wherein controlling polarization of the irradiating beam comprises controlling orientations of a half-wave plate, and a quarter-wave plate.

14. The method according to claim 12, wherein the polarization of the irradiating beam is chosen from one of a linear polarization, a circular polarization, and an elliptical polarization.

15. The method according to claim 12, and comprising, prior to the optimizing, calculating a mean and a standard deviation of the signals generated by each detector, and calculating a signal-to-noise ratio (SNR) for each detector in response to the mean and the standard deviation.

16. The method according to claim 15, and comprising, prior to the optimizing, receiving reference signal values generated by a non-polarizing defect, and wherein calculating the SNR comprises calculating the SNR in response to the reference signal values.

17. The method according to claim 15, and comprising, prior to the optimizing, generating multiple SNR values in response to multiple polarizations of the irradiating beam, and in response to respective orientations of each analyzer, and determining a sum of the multiple SNR values.

18. The method according to claim 17, and comprising, prior, to the optimizing, determining a maximum value of the sum, and in response thereto determining an optimized illumination polarization setting for the irradiating beam, and a respective optimized setting for each analyzer.

19. The method according to claim 12, and comprising detecting a defect on the surface by directing the optics to irradiate the surface at an adjusted polarization, and by setting orientation of each of the analyzers.

20. A method for determining irradiation parameters for a surface, comprising:
    operating an irradiation system to irradiate the surface, the system comprising an illumination source, a first adjustable polarizer disposed between the source and the surface, a bright field detector and a respective bright field analyzer, the bright field detector positioned and adapted to generate bright field signals in response to light specularly reflected from the surface and received via the bright field analyzer, a plurality of gray field detectors, each adapted and positioned to generate gray field signals in response to light reflected from the surface within a first angular region and received via a gray field analyzer associated with the gray field detectors, and one or more dark field detectors, each adapted and positioned to generate dark field signals in response to light reflected from the surface within a second angular region and received via one or more respective dark field analyzers;

operating a controller responsive to the bright field signals, gray field signals and dark field signals to optimize settings for each detector and analyzer and to compute a respective score indicative of each of the settings; and selecting and setting one set of the settings for use in inspection of the surface with the system.

21. The method according to claim 20, wherein computing the respective score comprises calculating a plurality of signal-to-noise ratios (SNRs) for the bright field, gray field and dark field signals and determining a sum of the SNRs.

22. The method according to claim 21, and comprising determining a maximum value of the sum, wherein selecting one set of the settings comprises selecting the set of the settings in response to the maximum value.

23. Apparatus for determining irradiation parameters for a surface, comprising:

an illumination source having a first adjustable polarizer disposed between the source and the surface;

a bright field detector and a respective bright field analyzer, the bright field detector positioned and adapted to generate bright field signals in response to light specularly reflected from the surface and received via the bright field analyzer, a plurality of gray field detectors, each adapted and positioned to generate gray field signals in response to light reflected from the surface within a first angular region and received via a gray field analyzer associated with the gray field detectors, and one or more dark field detectors, each adapted and positioned to generate dark field signals in response to light reflected from the surface within a second angular region and received via one or more respective dark field analyzers;

a controller responsive to the bright field signals, gray field signals and dark field signals and adapted to:

optimize settings for each detector and analyzer, compute a respective score for each set of the settings, and select one set of the settings for use in inspection of the surface.

24. The apparatus according to claim 23, wherein the first adjustable polarizer comprises an adjustable half-wave plate and an adjustable quarter-wave plate.

25. The apparatus according to claim 23, wherein the analyzers comprise adjustable polarizers.

26. The apparatus according to claim 23, wherein the controller is adapted to calculate a plurality of signal-to-noise ratios (SNRs) for the signals, and determine a sum of the SNRs.

27. The apparatus according to claim 26, and wherein the controller is adapted to determine a maximum value of the sum, and to select the one set of the settings in response to the maximum value.

* * * * *